United States Patent [19]

Bianchi et al.

[11] Patent Number: 4,795,539
[45] Date of Patent: Jan. 3, 1989

[54] SYSTEM AND USE THEREOF FOR COLLECTING CHEMICAL-PHYSICAL, ELECTROCHEMICAL AND MECHANICAL PARAMETERS FOR DESIGNING AND/OR OPERATING CATHODIC PROTECTION PLANTS

[75] Inventors: Giuseppe Bianchi, Milan; Gian L. Mussinelli, Lomazzo; Bruno Bazzoni, Milan, all of Italy

[73] Assignee: Oronzio de Nora S.A., Lugano, Switzerland

[21] Appl. No.: 839,414

[22] Filed: Mar. 13, 1986

[30] Foreign Application Priority Data

Mar. 13, 1985 [IT] Italy ............................. 19877 A/85

[51] Int. Cl.$^4$ ............................. C23F 13/00
[52] U.S. Cl. ............................. 204/147; 204/196; 204/435; 324/65 CR; 324/65 R
[58] Field of Search ............... 204/147, 196, 407, 412, 204/431, 433, 404, 435; 166/250, 336, 902; 405/157, 211; 324/65 CR, 65 R

[56] References Cited

U.S. PATENT DOCUMENTS

| | | | |
|---|---|---|---|
| 2,793,527 | 5/1957 | Turner, Jr. et al. | 324/65 CR |
| 3,632,495 | 6/1969 | Watson et al. | 204/404 |
| 3,748,247 | 7/1973 | Weisstuch | 324/65 CR |
| 4,395,436 | 7/1983 | Bianchi et al. | 427/53.1 |
| 4,452,683 | 6/1984 | de Nora et al. | 204/196 |
| 4,526,666 | 7/1985 | Bianchi et al. | 204/196 |
| 4,535,843 | 8/1985 | Jageler | 166/250 |
| 4,587,479 | 5/1986 | Rhoades et al. | 324/65 CR |

Primary Examiner—John F. Niebling
Assistant Examiner—Ben C. Hsing
Attorney, Agent, or Firm—Pollock, Vande Sande & Priddy

[57] ABSTRACT

System for collecting chemical-physical and electrochemical parameters for designing and/or operating cathodic protection systems applied to steel structures exposed to corrosion. The system includes a series of electrode sensors (5, 6), (5–7, 5–7'), (14–16), (17), connected to conducting sleeves (2) applied onto a multipolar conducting cable (1) and/or series of conventional sensors placed in sealed rooms (26) provided inside cable (1).

The invention further discloses the method for utilizing said apparatus.

2 Claims, 9 Drawing Sheets

SYSTEM AND USE THEREOF FOR COLLECTING CHEMICAL-PHYSICAL, ELECTROCHEMICAL AND MECHANICAL PARAMETERS FOR DESIGNING AND/OR OPERATING CATHODIC PROTECTION PLANTS

FIELD OF THE INVENTION

1. Description of the Invention

The present invention relates to a system and the use of the same for collecting chemical-physical and electrochemical parameters useful for designing and/or operating cathodic protection systems applied to steel structures exposed to corrosive environments, either natural (sea-water, fresh and brackish waters, ground) as well as industrial (solutions or wet solids inside pipes, tanks, apparatuses).

Upon defining the application field of the invention, the following description will refer to specific embodiments for sea-water applications. These embodiments, however, are not to be intended as a limitation of the present invention but substantially constitutes representative examples of the applicability of the same.

2. Background of the Invention

As a matter of fact, in the last two decades, the use of structures operating in sea water environments has achieved an ever increasing importance. A well-known example is represented by the platforms in the North Sea for prospecting and exploiting oil fields. These structures most often operate under severe conditions and therefore strict reliability requirements are to be met.

As it is well known, a steel structure exposed to sea water is subject to rapid corrosion (0.1–0.5 mm/year) and consequently, if no protection is provided, its operating lifetime is limited to a few years.

Corrosion is mainly due to the the presence of oxygen which is dissolved in sea water in an apparently negligeable quantity (about 10 mg/liter) but sufficient to represent a problem in this regard.

In order to protect steel against corrosion, a protective coating insulating steel from water may be resorted to. However, said coating, generally constituted by an organic polymeric material, is not completely impermeable to water and oxygen. Further, it may be damaged due to mechanical injuries or detached due to abrasion, the underlaying steel resulting thus exposed to corrosion. Furthermore, the coating is subject to degradation with time and periodical maintenance is required.

For the above reasons, a protective coating alone cannot overcome the problems of corrosion of steel structures in sea water applications, especially in the case of deep water off-shore structures, wherein maintenance represents a serious difficulty. In fact, an active life-time longer than five-ten years could not be granted by resorting to such a solution.

The most efficient solution to the above problems is represented by cathodic protection, which is the field of the present invention.

In this case, electrons are fed to the steel structure by means of an electric circuit in a quantity corresponding to the quantity of oxygen contacting the steel surface. The consequent oxygen reduction reaction produces hydroxyl ions:

$$O_2 + 2H_2O + 4e \rightarrow 4OH^-$$

Corrosion of the steel structure due to oxygen is thus inhibited.

The evalutation of the quantity of oxygen contacting the steel surface is instrumental in order to determine the critical value of current density required for a complete cathodic protection. In fact, if the current density is below critical value, the quantity of oxygen in excess gives rise to corrosion phenomena, while with higher values of current density, hydrogen is evolved at the steel surface, which may cause embrittlement of the steel, especially under low frequency fatigue conditions.

In the case steel is protected by a coating, a reduced quantity of oxygen contacts the steel surface and consequently also the current density necessary to cathodically protect the structure results reduced. In the case of sealines, wharfs, and the like, protection against corrosion is obtained by means of a protective coating and a supplementary cathodic protection system; allowing thus for an operating lifetime of at least twenty of thirty years.

Steel results unaffected by the corrosive action of oxygen in sea water when a potential value lower than −0.800 V, versus a silver-silver chloride reference electrode, is provided. Embrittlement of steel may occurr when the potential is lower than -1.050 V, while the current density may vary within an ample range depending on the quantity of oxygen which, under the various operating conditions, contacts the structure surface.

In the case of off-shore structures, abrasion due to the presence of sand would readily damage the coating. Therefore, steel is protected against corrosion, especially in deep water (wherein repairing of damages to the coating results prohibitive), by resorting to cathodic protection systems applied on the uncoated steel structure.

The current density may vary within ample limits (in the range of 0.05–0.5 A/m2) depending on the geographical position, climate, sea conditions and on the geometry of the structure to be protected which may comprise elements more or less exposed to the corrosive action of sea water, depending also on the depth whereat said elements are positioned.

Furthermore, when current is fed to the structure to be protected by means of sacrificial anodes (Zn, Al) electrically connected to the structure, the cathodic protection system results self-regulating, that is, the potential value remains within the safety range.

When designing a sacrificial anode cathodic protection system, besides the characteristics of the anodes, the following data are to be taken into account:

(1) current density under the most unfavourable conditions. This value is necessary in order to determine the minimum amount of sacrificial anodes.

(2) average protection currect density detected over a sufficiently long period of time as to be representative, in order to determine the weight of the sacrificial anodes and thus ensure the granted operating life-time.

Due to the alkalinity caused by the cathodic reduction of oxygen, a layer of calcium carbonate and magnesium hydrate precipitates onto the structure surface. This layer acts as a protective coating and thus a considerably reduced quantity of oxygen can contact the structure surface. Consequently the current density required by the cathodic protection systems is comparably reduced.

However, this protective layer may be periodically detached, for example by sea storms, and consequently the cathodic protection systems has to be dimensioned in order to ensure that the layer is readily reformed as soon as possible.

When cathodic protection is effected by the impressed current method, that is an external electric circuit is connected to a power supply and utilizing insoluble anodes (for example platinized titanium or noble metal activated titanium anodes) placed in proximity of the steel structure to be protected, the cathodic protection systems has to be dimensioned on the basis of the maximum current density value. In this case, three considerations have to be taken into account:

(1) the cathodic protection system is not self-regulating and the insoluble anodes, each one connected to the power supply by means of a cable, are in a limited number with long current lines between the anode and the structure to be protected. The consequent ohmic losses may cause overprotection when the steel potential results too much negative, involving embrittlement of steel.

(2) the cathodic protection system may be controlled suitably adjusting the current supply if the situation as regards the current density and the protection efficiency of the calcium carbonate - magnesium hydrate layer is monitored.

(3) Due to the limited number of anodes, the risk exists that the steel surface in proximity of the anodes are overprotected, while the steel surfaces which are shielded or far from the anodes may remain underprotected. The protective layer of calcium carbonate-magnesium hydrated performs a fundamental function on providing for an even protection if the anode position has been optimized with respect to the structure geometry. Models and numerical programs may be advantgeously utilized to study the electric field sorrounding the structure and suitably position the anodes or otherwise, with respect to a fixed position of the anodes, advantageously determine the total protection current necessary to provide for the most uniform distribution of current.

The complexity of the various factors affecting the cathodic protection system results evident from the foregoing and consequently the necessity of an evaluation of the same, either during the designing phase as well as during operation of the system, in order to optimize the efficiency thereof by suitably controlling the impressed potential and the protection current.

SUMMARY OF THE INVENTION

It is therefore the main object of the present invention to provide for a system and method for detecting and controlling these parameters.

The present invention provides for a system for collecting chemical-physical and electrochemical parameters such as pH, dissolved oxygen concentration, resistivity, temperature and for determining the cathodic polarization curve for oxygen reduction as well as the kinetics regarding formation of the protective layer of calcium carbonate-magnesium hydrate as well as their evolution with time (e.g. with respect to thickness, composition, compactness).

The system may be installed on the site wherein the structure to be protected will be installed (wharf, platform, pipeline or the like) in order to collect the necessary data for a sufficiently long time (for example, one year).

Alternatively, the system may be installed also in proximity of an existing structure cathodically protected by the impressed current method, in order to collect and transmit the data necessary for an automatic continous control of the power supply unit or units.

Furthermore, the present invention provides for a method for collecting and analyzing the above mentioned data and parameters and for automatically controlling the cathodic protection system.

According to the present invention, the required data are collected in a simple, direct and continuous way without the need to resort to frequent inspections or surveys, uneasy and troublesome, especially in sea-water applications. In fact, at present, divers or underwater vehicles have to be utilized.

An improved efficiency is achieved by monitoring the cathodic protection system in a careful, reliable way.

The system according to the present invention comprises a series of sensors assembled onto a multipolar cable constituted by an electrically conductive internal strand, exhibiting good mechanical characteristics, at one end of which an anchoring metallic hook is connected by means of an electrically insulated and hydraulically sealed coupling. An array of insulated electrically conducting wires is placed around the strand, in a suitable number depending on the number of sensors.

The strand and wires circular array are covered by a sheath, substantially cylindrical, made of a resilient insulating material, such as rubber. Therefore, the strand-wire array-sheath assembly looks like, and is in fact similar to, an electrical cable.

Metal sleeves are disposed along the cable length, at suitable intervals. These sleeves have an internal diameter slightly larger than the cable diameter. Hydraulic sealing, efficient also in deep water, is provided by means of suitable resins or rubber cements. Alternatively, an insulating green rubber compound, resistant to chlorine, may be injected through suitable threaded holes provided in the sleeves. These holes are then closed by a cap. This compound is then vulcanized after assembling. Another known method to provide the sealing may consist in plastically inwardly deforming the end portions of the sleeve by means of a suitable tool (see Italian Patent application No. 21754 A/83 by the same applicant of the present application).

The sensors for measuring the chemical-physical, electrochemical or any other required parameter are positioned in correspondence with the metal sleeves and electrically connected to conventional monitoring units by means of the electrically conducting wires disposed around the strand.

The sensors and relevant electrical connections are installed in different ways depending on the type of measurement. The electrode sensors suitable for measuring potential, pH, resistivity, oxygen concentration, are usually in the form of a ring applied onto the metal sleeves, typically made of titanium. Conversely, thermometers, hydrometers, strain gauges, devices for measuring electric current, magnetic flux, oscillations, vibrations, displacements due to waves or sea currents are most advantageously contained in hollow sealed housings which are provided by stripping off the insulating sheath and placing, in correspondence of the two split surfaces, substantially annular clamping elements abutting against split surface and constituted by a collar diametrally split in two halves, having the same external diameter as the insulating sheath and the internal diameter slightly larger than the diameter of the conducting wire circular array.

The two halves of the split collar are connected by plugs in order to form a circular bush after assembly.

Each of the two bushes, made of steel or other suitable resistant materials, abuts against the relevant annular split surface of the insulating rubber sheath and defines a circular hole for the passage of the connecting wires.

A metal sleeve inserted onto the cable at the stripped off portion of the sheath and longer than stripped off sheath portion and having a diameter slightly larger than the insulating sheath, laterally defines the annular room destined to receive the sensors. In order to clamp sleeve to the cable, the sleeve is then plastically inwardly deformed at each of the two bushes. Hydraulic sealing between sleeve and sheath may be provided, by pouring or injecting resins, rubber cement, green rubber, then vulcanized, or plastically inwardly deforming the end portions of the sleeve.

The type and geometry of the electrode sensors connected to the system depend on the specific application. Particularly, at least three different types of electrode sensors may be provided, according to the present invention. A first embodiment comprises an electrode, or preferably a couple of electrodes consisting of an activated valve metal electrode and a reference electrode, made for example of silver/silver chloride, confined between insulating shields apt to exactly define the electric and diffusive field. In a second embodiment a sensor is provided which is suitable for determining the evolution with time of the protective calcium carbonate-magnesium hydrate layer onto a cathodically polarized metal (for example steel) at a predetermined potential. Said sensor is constituted by two electrodes of said metal and by two reference electrodes provided with shields for defining the electric and diffusive field. In a third embodiment, a high current capability electrode made of an activated valve metal, which may act either as a high current capability anode or as a second electrode for measuring the electric conductivity of sea water or as cathode during particular experimental phases.

The reference electrodes of the first two types of sensor are coplanar with the energized electrodes and are positioned in a side annular recess defined by said insulating shields as to intercept the equipotential surfaces close to the polarized electrode surface and to minimize the contribute of the ohmic drops in the readings. Suitable reference electrodes may be constituted for example by Ag/AgCl or Zn rings applied onto a valve metal tube whose exposed surface acts as cathode and provides for a little anodic polarization of the reference electrode so that the surface thereof is maintained activated.

Periodical anodic polarizations of the valve metal surfaces inhibit formation of scales or fouling.

By utilizing the three types of sensors above described, which are connected to the insulated wires surrounding the strand, the cathodic polarization curve of oxygen may be detected as well as the oxygen concentration through the oxygen diffusion limiting current. Water resistivity is determined by measuring the resistivity in alternate current between two activated valve metal electrodes, while the kinetics of the growth of the protective layer of calcium carbonatemagnesium hydrate under various cathodic potentials are determined by measuring resistance changes. Specific examples are hereinafter described in detail.

Another type of sensor for measuring the pH may be provided, which is constituted by a metal ring, for example of antimony or alloys thereof, applied onto a valve metal sleeve whose exposed surface are protected by an insulating coating and a reference electrode as previously described.

The number and type of sensors according to the present invention, connected to the respective wires of the wire array, will susbtantially depend on the necessary or required measurements. For example, some of the above illustrated sensors may be omitted in the case the corresponding parameters are already known or are not significant as regards the plant to be monitored or designed.

Even one single sensor may be foreseen. However, according to a preferred embodiment, the system of the present invention comprises the aforementioned three different types of electrodes, as well as a sensor for measuring the pH and one for the temperature, which sensors allow for monitoring the most important and instrumental data.

The wires of the wire array surrounding the strand are connected to a monitoring unit, which may be positioned either onto the structure to be protected or onto a floating buoy or may be held underwater. Said monitoring unit comprises a power supply source, an automatic control circuit for the different funtional sequences (measurement, polarization, etc.), measuring circuits, a processor and a measurements data storage system, or, in the case the monitoring unit is out of reach or poses problem for the inspection, a telemetering system.

The monitoring unit components are of the conventional type, available on the market and well-known to the expert of the art and therefore no further description of the same is reported.

The dimensions of the system according to the present invention are not particularly critical and mainly depend on the geometry of the structure to be monitored. Typically, the insulating electric cable has a length varying from some meters up to several hundreds of meters with a thickness comprised between 10 and 200 mm. The metal sleeves have a diameter comprised between 0.5 and 2 mm, while their length may vary between some decimeters up to a couple of meters. Said sleeves may be of titanium as aforementioned, as well as of iron, copper or alloys thereof, stainless steel, valve metal, graphite, cast magnetite.

The reference electrodes may be of silver-silver chloride, zinc, amalgamated gold and the like. Similarly, the sensor for measuring the sea water pH may be a palladium electrode subjected to a weak cathodic intermittent polarization, or, as aforementioned, an antimony alloy electrode.

As mentioned above, sealing between the cable and the metal sleeves may be provided through different methods, the most common being the injection or pouring of resins (for example epoxide) or rubber cement (for example silicone) to fill the thin interstice between the insulating sheath and the internal surface of the cables. As an alternative, a thermosetting plastic sleeve may be applied, having a length of 10–40 cm and overlapping the metal sleeve for a length of 5–20 cm.

Electrical contact between a metal sleeve and one of the wires may be provided in a known way by means of an elastic, radially expandable, metal element.

The invention will be hereinbelow described making reference to the attached drawings, which are intended only to illustrate the invention and not to limit the same. Referring to the figures:

BRIEF DESCRIPTION OF THE FIGURES

FIG. 7b shows a transversal cross-sectional view taken along line IV—IV of FIG. 7a.

DESCRIPTION OF THE PREFERRED EMBODIMENT

In the Figures the reference numeral 1 indicates the insulated cable constituted by the inner electroconductive strand 9 and a circular array 10 of insulated electroconductive wires 11, surrounded by a a sheath 12 made of electrically insulating, resilient material, such as rubber. A sleeve 2 made of a metallic material (e.g. titanium, copper) or graphite, and coaxial to the cable 1 is clamped and hydraulically sealed to cable 1 in a way as mentioned above.

Figure 1:
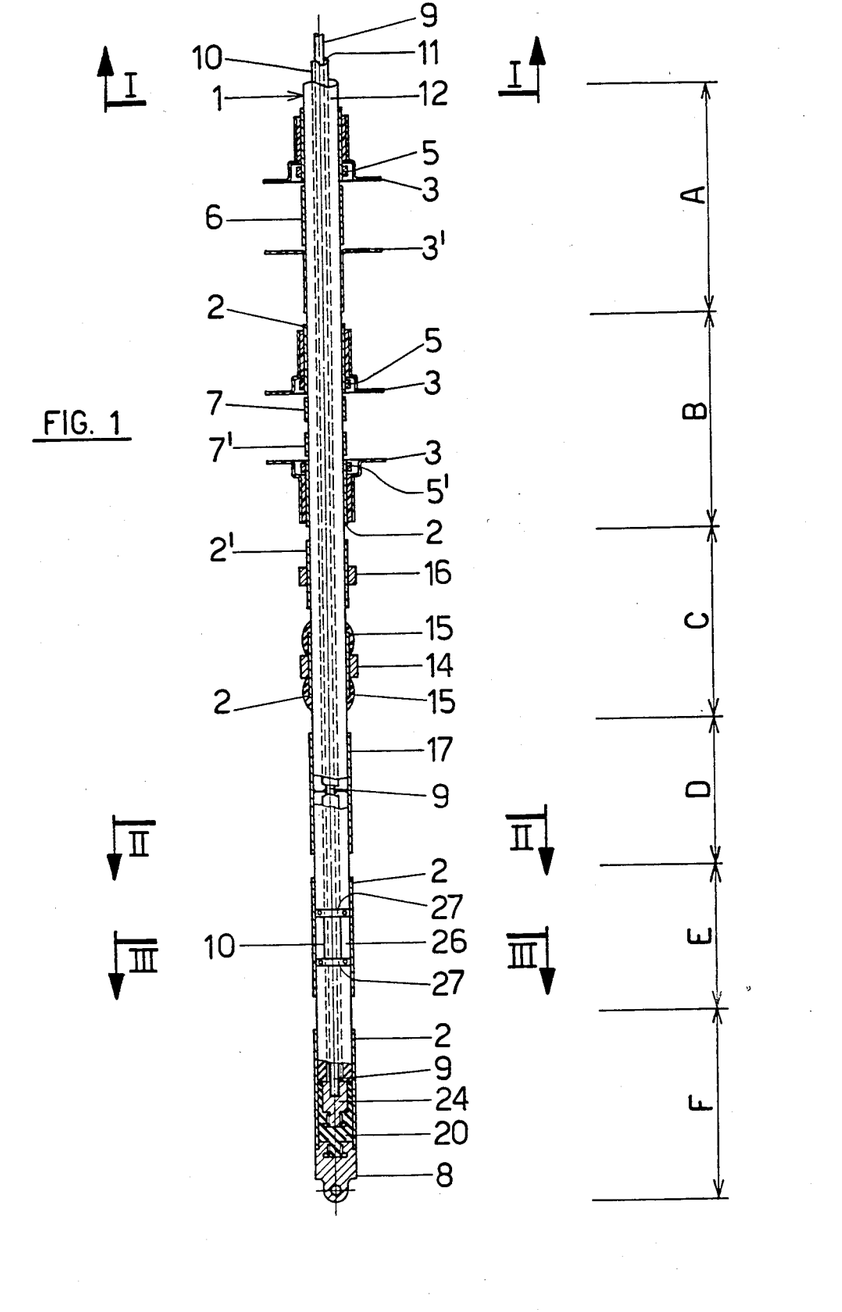
FIG. 1 shows a longitudinal cross-sectional view of an embodiment of the present invention, provided with six meaurement sections (A,B,C,D,E, and F).

In FIG. 1, sections A, B, C and D define the position of the different types of sensors. Section A corresponds to a sensor constituted by two insulating shields 3 and 3' (see FIG. 3), for example made of anodized or coated titanium, or plastic material, suitable for defining the electric and diffusive field and coaxially fixed onto metal sleeve 2 and to cable 1 respectively. An electrically insulating filling layer 13 is interposed between shield 3 and the sleeve 2. Conversely, shield 3' contacts directly the cable 1. The shield 3 constitutes an annular recess 4 wherein a reference electrode 5 made of silver-silver chloride is positioned. The reference electrode 5 is constituted by a silver ring directly contacting the sleeve 2.

Figure 3:
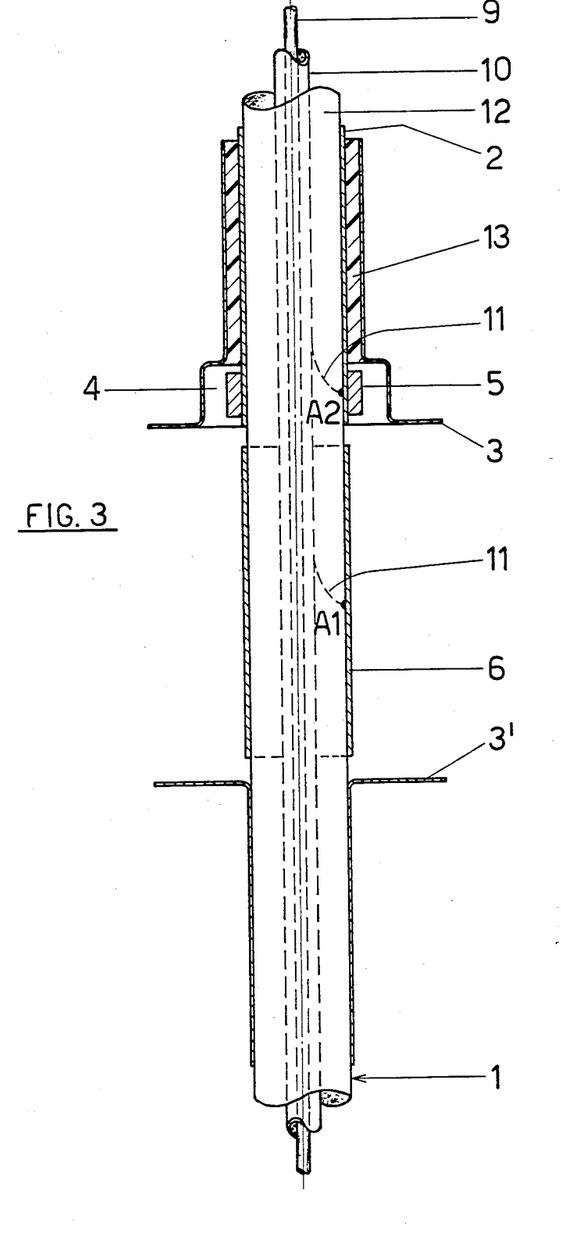
FIGS. 3 to 6 are enlarged views respectively of sections A, B, C and D of FIG. 1, which sections are provided with a different type of sensor.

A sleeve 6, constituted by an activated valve metal, is directly fixed onto the insulated cable 1 and electrically connected by one of the wires 11 to the monitoring and power supply unit (not illustrated).

Section B of FIG. 1 corresponds to a second type of sensor and the same reference numerals are used to designate the same elements as in Section A. The electrode is constituted (FIG. 4) by two steel sleeves 7 and 7', spaced apart and fixed onto the cable 1. Each sleeve is electrically connected as for electrode 6 to a respective wire 11.

Figure 5:
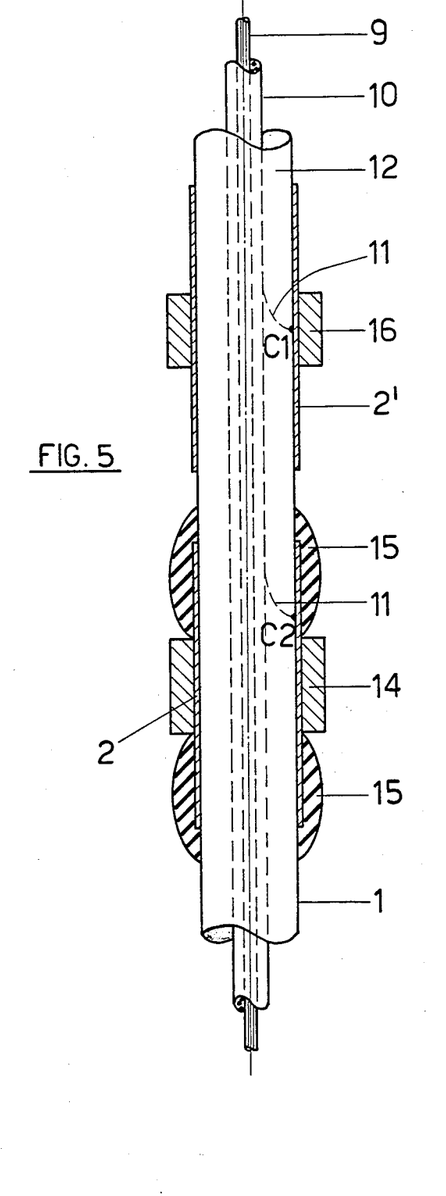
Figure 6:
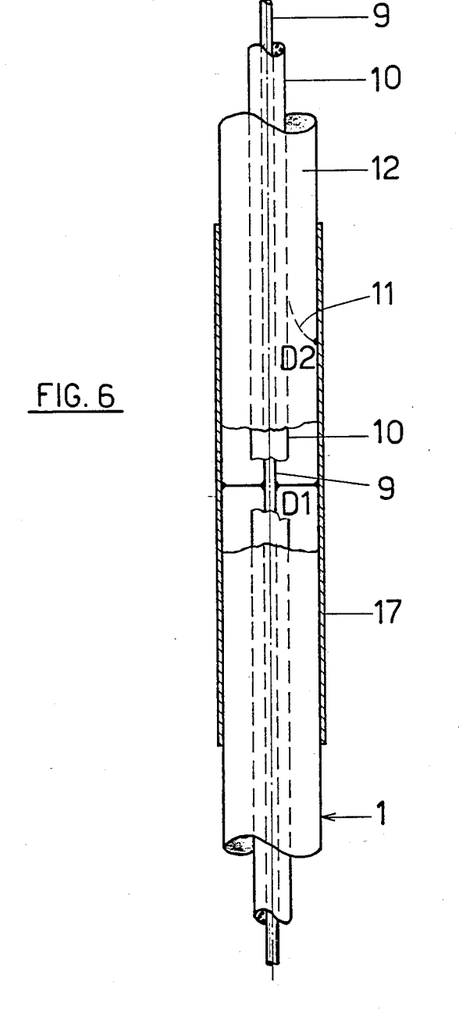
Figure 7A:
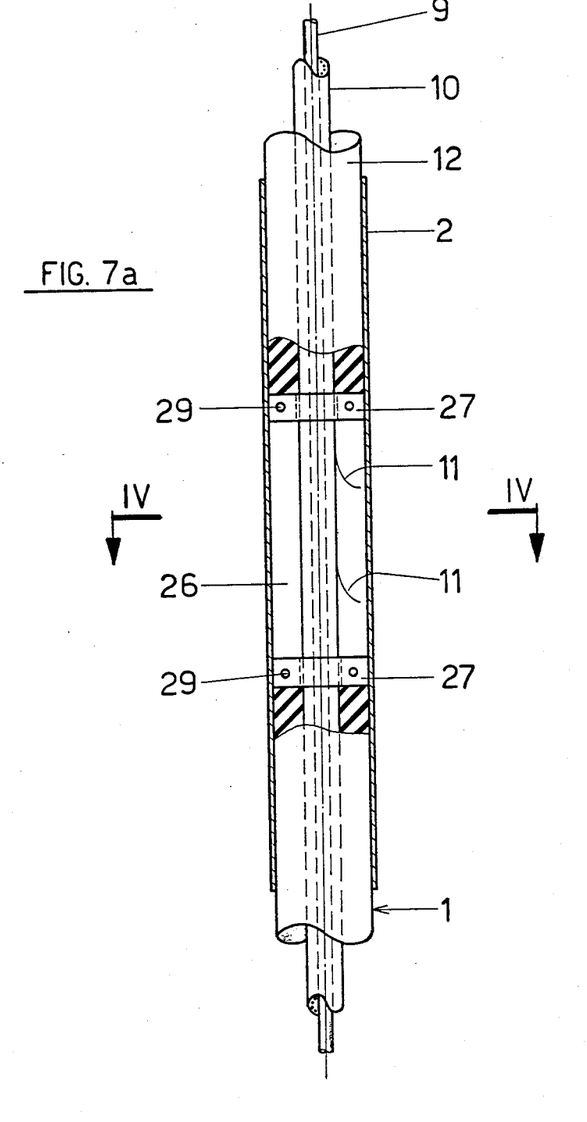
FIG. 7a shows a longitudinal cross-sectional view of a hydraulically sealed housing, (section E of FIG. 1,) for a known sensor or sensors (not illustrated in the Figure) to be maintained in an hydraulically sealed room.

Sections C, D and E of FIG. 1 correspond respectively to a sensor for pH measurement, a high current capability electrode and the sealed housing containing a sensor, which will be illustrated in greater detail in FIGS. 5, 6 and 7 respectively.

Lastly, in section F of FIG. 1 the terminal anchoring and drawing hook of the system according to the present invention is illustrated. This terminal hook is illustraed in greater detail in FIG. 8.

Figure 2A:
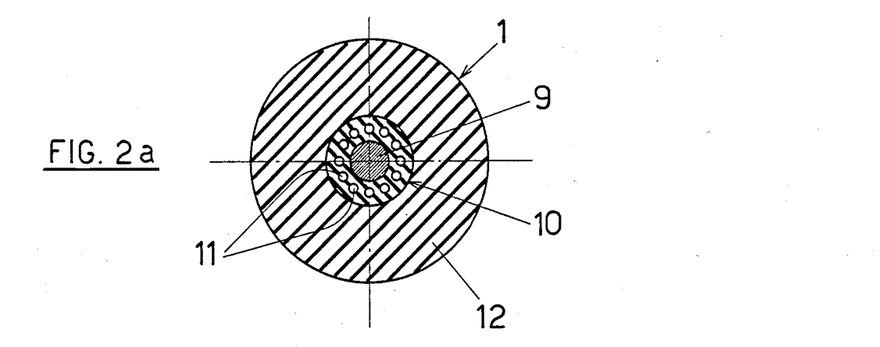
FIG. 2a is a transversal cross-sectional view taken along line I—I of FIG. 1.

FIG. 2a, illustrates the typical transversal cross-sectional view of the cable 1, including the inner electroconductive strand 9, surrounded by the circular array 10 of electrically insulated wires 11, whose number depends on the required number of connections to the sensors.

Figure 2B:
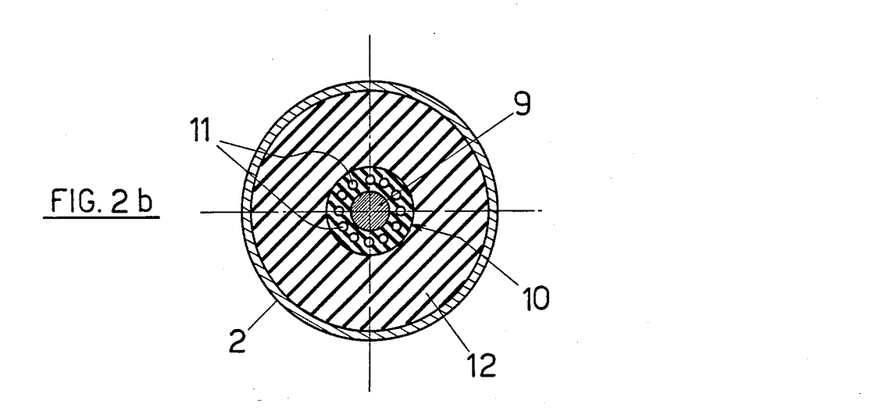
FIG. 2b shows a transversal cross-sectional view taken along with line II—II of FIG. 1.

FIG. 2b illustrates the typical transversal cross-sectional view of the system according to the present invention at a point in which a metal sleeve is provided, and shows the inner strand 9, the circular array 10 of electrically insulated wires 11, the rubber sheath 12 and the metal sleeve 2, electrically connected to one of the wires 11.

Figure 2C:
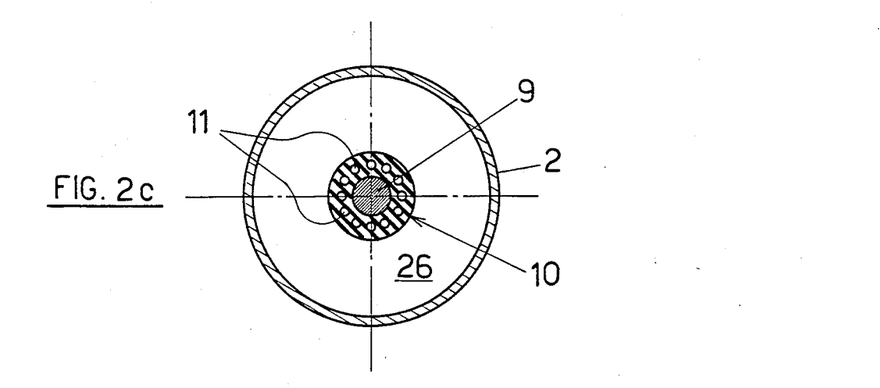
FIG. 2c shows a transversal cross-sectional view taken along lines III—III of FIG. 1.

FIG. 2c, illustrates a typical trasversal cross-sectional view of a hydraulically sealed housing for the physical sensors, and shows the inner strand 9, the circular array 10 of electrically insulated wires 11, the metal sleeve 2 and the sealed room 26 for the physical sensors electrically connected to wires 11.

FIG. 3 illustrates in greater detail Section A of FIG. 1. In this figure as well as in the following ones, the same reference numeral designate the same parts. The electrical connection between one of the wires 11 and the electrode 6 is indicated by A1, while A2 indicates the connection between another wire 11 and reference electrode 5. The reference numeral 13 indicates the electrically insulating filling layer between the shield 3 and the metal sleeve 2. The silver ring 5 is connected to one of wires 11 through the sleeve 2.

Figure 4:
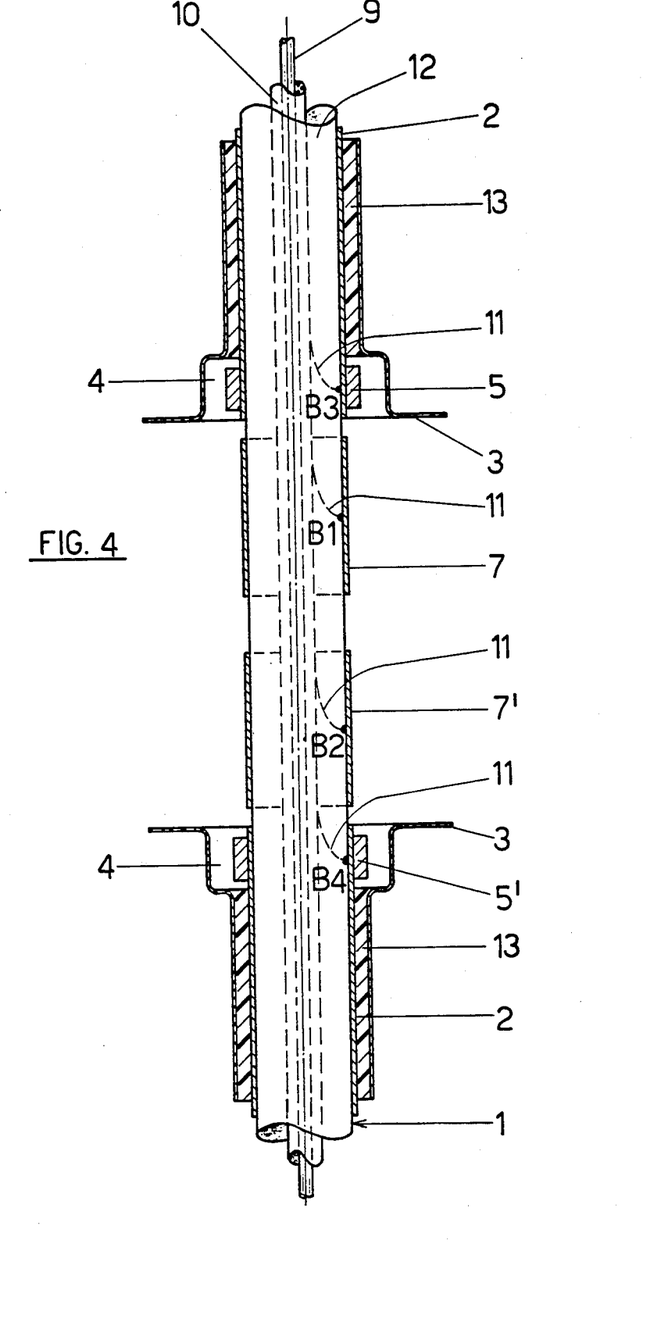

FIG. 4 illustrates in greater detail section B of FIG. 1. Each electrode 7, 7', constituted by steel or activated valve metal, is electrically connected to a distinct wire 11 (the connections being indicated by B1 and B2 respectively). A reference electrode 5 and 5' for each electrode 7, 7' is provided in an annular recess 4 formed by the shield 3, in order to minimize the ohmic drops contribution to the measured values. Each reference electrode 5 and 5' is in turn connected to relevant other wires 11 (connections B3 and B4 respectively).

FIG. 5 refers to Section C of FIG. 1, wherein an electrode for pH measuring is positioned. Said electrode is constituted by a ring 14 of antimony or alloys thereof and is applied onto a first conductive sleeve 2 covered by an insulating thermosetting material 15 on the two sides of said ring 14. One of the wires 11 is connected to sleeve 2 which is electrically connected to antimony ring 14, the connection being indicated by C2. Similarly, a reference electrode consisting of a silver ring 16 is applied onto a second conductive sleeve 2', adjacent to the first one, and is connected to a single wire 11, the connection being indicated by C1.

FIG. 6 refers to section D wherein the high current capability activated titanium electrode 17 is directly electrically connected to the inner strand 9 (the connection point being indicated by D1), while a second connection D2 to another wire 11, which wire is not subject to current flow and ohmic losses, is provided for measuring purposes.

FIG. 7a illustrates a typical hydraulically sealed housing for a sensor or sensors (either mechanical, physical or similar) requiring for hydraulical sealing. Room 26 is laterally defined by the metal sleeve 2 and, at each of its ends, by two bushes 27, in contact with the split surfaces of the insulating sheath 12, a proper section of which has been previously stripped off. The two bushes 27 define a circular hole 29 for the passage of the inner strand 9 and circular array 10 of wires 11, to which the sensor or sensors placed into the housing are electrically connected. Plastically deforming of the metal sleeve 2 inwardly in correspondence of the two bushes 27 allows for fixing said bushes to the sleeve, thereby clamping the sleeve to the cable 1.

Figure 7B:
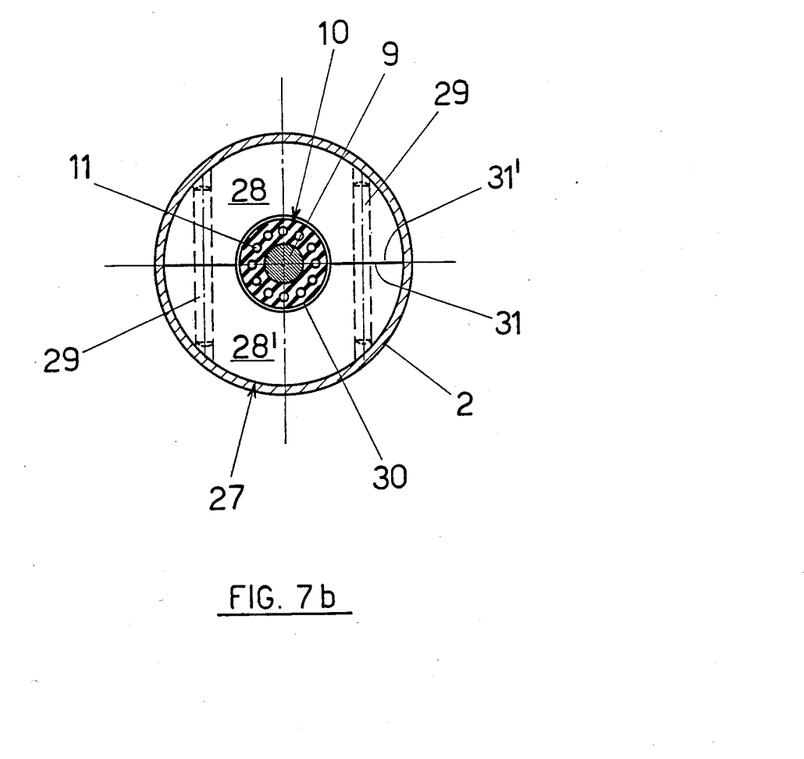

FIG. 7b shows bushes 27, consisting of two half-bushes 28 and 28' provided with plugs for joining of the same and delimiting hole 30 once the diametral surfaces 31 and 31' are pressed together by squeezing external sleeve 2.

Figure 8:
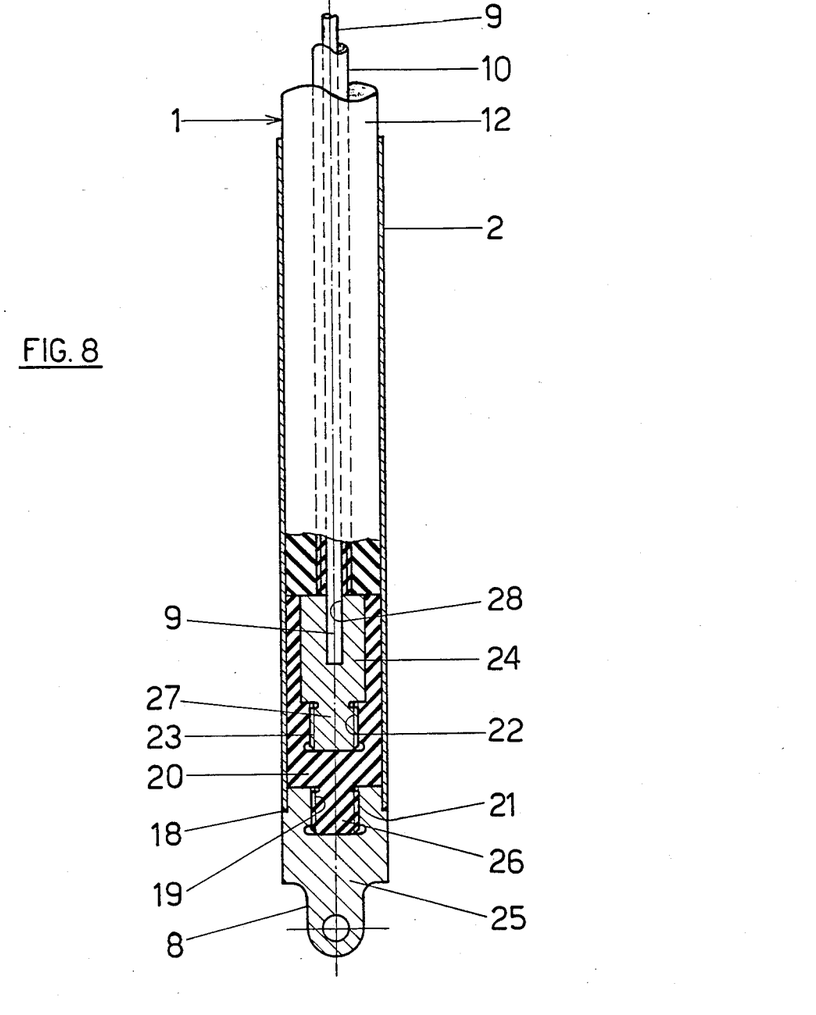
FIG. 8 shows a detail of the anchoring and drawing hook of section F in FIG. 1.

FIG. 8 shows the end portion of the system according to the present invention, comprising an eyelet 8, and a cylindrical body 25 of a material resistant to water corrosion (for example titanium monel or hastelloy), said cylindrical body 25 having substantially the same diameter of sleeve 2 inserted onto one end of cable 1. The cylindrical body 25 is coaxial to sleeve 2 and is welded to one end of said sleeve 2. The welding connection is indicated by reference numeral 18 in the figure. The cylindrical body 25 is provided with a threaded dead hole 19 suitable for engaging a corresponding threaded coaxial stem 26 of a bush 20, made of a substantially rigid, electrically insulating material, such as Babllite or a ceramic material. Bush 20 is in turn provided with a threaded dead hole 22 suitable for engaging a threaded coaxial stem 27 of a metal bush 24. Said bush 24 is provided with a threaded coaxial dead hole 28 opposite to said stem 27, thereby allowing for blocking one end of strand 9 by means of a known technique, for example by squeezing the upper portion of said bush 24.

The sealing between the upper end of sleeve 2 and cable 1 is provided, for example by injecting resin, or rubber cement, or green rubber which is then vulcanized, or by applying a thermosetting coupling, or also by plastically inwardly deforming the terminal portion of said sleeve 2. An efficient hydraulic sealing is so provided also in deep waters, but other equivalent solutions may be obviously resorted to.

The above illustrated system, used together with conventional monitoring systems, may be utilized during the various operating phases. Different circuit layout may be utilized depending on the various applications.

Under a preliminary phase, the proper operation of the reference electrodes may be assessed by applying anodic polarization under very low current density and comparing the reference electrode potentials two by two, the other sensors being electrically disconnected. Anodic polarization to electrical connections A1 (FIG. 3) and D1 (FIG. 6) may be applied versus electrical connections B1 and B2 (FIG. 4) acting as cathodes, so that the surface of the activated titanium electrodes results thus clean, free from scales and fouling.

By applying cathodic polarization of electrical connection A1 (FIG. 3) versus D1 (FIG. 6) and detecting the potential by means of electrical connection A2, the potential polarization curve for cathodic reduction of oxygen and the oxygen diffusion limiting current density are obtained.

Similarly, through a slow recording, the kinetics of formation of the protective coating of calcium carbonate-magnesium hydrate may be determined.

Further, the electrical resistance of electrical connection A1 (FIG. 3) versus D2 (FIG. 6) may be determined under alternate current at regular time intervals.

Dissolution of said protective coating formed onto the structure con be detected by anodic polarizing the electrical connection A1 (FIG. 3) versus electrical connection D1 (FIG. 6) and then measuring the electric resistance between A1 and D2 at regular time intervals.

Furthermore, the electrical resistance of electrical connection A1 versus D2 may be detected in order to determine, by calibration, the electrical resistivity of sea water. The temperature value allows to determine the sea water salinity.

Lastly by applying cathodic polarization to electrical connections B1 and B2 (FIG. 4) versus D1 (FIG. 6) under a monitored potential by utilizing electrical connections B3 and B4 (FIG. 4), the evolution of said protective coating may be determined by means of periodical measurement of resistance under alternate current between electrical connections B1 and B2 (FIG. 4).

It has to be understood that the foregoing description refers to some embodiments of the system of the present invention. All possible modifications which are obvious to a person skilled in the art, also as concerns the method for collecting chemical-physical, electrochemical and similar parameters useful for designing and/or operating cathodic protection systems, which is a further object of the present invention, may be made without departing from the scope thereof.

We claim:

1. A device for measuring current density corresponding to the limiting oxygen diffusion rate towards the surface of a metal structure to be cathodically protected comprising:

a test electrode, an auxiliary electrode, and a reference electrode, all inserted onto a multipolar electric cable and spaced along said cable length;

said test electrode including a valve metal sleeve, said sleeve being electrically connected (A1) to a wire of said multipolar cable, said auxiliary electrode including a valve metal sleeve, said sleeve being electrically connected (D1) to a wire of said multipolar cable;

said reference electrode being positioned in close proximity to the edge of said test electrode and including a valve metal sleeve inserted onto said multipolar electric cable and a silver or zinc ring applied onto said sleeve, said sleeve being electrically connected (A2) to a wire of said multipolar cable, wherein two non-conductive shields are positioned in close proximity to both edges of said test electrode to exactly define the electric and diffusing fields.

2. A reference electrode for measuring the electrochemical potential of cathodically protected structures comprising:

a valve metal sleeve inserted onto a multipolar electric cable and a metal ring made of silver or zinc, applied onto said sleeve, said sleeve being electrically connected (A2) to a wire of said multipolar cable, said reference electrode further comprising an auxiliary electrode inserted onto said multipolar electric cable, said auxiliary electrode including a sleeve made of an activated valve metal, said sleeve being electrically connected (A1) to a wire of said cable, wherein periodical anodic polarization is applied to inhibit formation of scales or fouling by means of an electric DC source applied between connections (A1) and (A2).

* * * * *